(12) United States Patent
Wooley

(10) Patent No.: US 9,940,769 B2
(45) Date of Patent: Apr. 10, 2018

(54) WEARABLE KEY FOB

(71) Applicant: Flextronics AP, LLC, Broomfield, CO (US)

(72) Inventor: George Michael Wooley, Troy, MI (US)

(73) Assignee: Flextronics AP, LLC, San Jose, CA (US)

(*) Notice: Subject to any disclaimer, the term of this patent is extended or adjusted under 35 U.S.C. 154(b) by 82 days.

(21) Appl. No.: 14/472,783

(22) Filed: Aug. 29, 2014

(65) Prior Publication Data

US 2016/0063777 A1    Mar. 3, 2016

(51) Int. Cl.
*G08C 19/00* (2006.01)
*G07C 9/00* (2006.01)
*A61B 5/00* (2006.01)

(52) U.S. Cl.
CPC ............ *G07C 9/00944* (2013.01); *A61B 5/00* (2013.01); *A61B 5/681* (2013.01); *A61B 2560/045* (2013.01); *G07C 2009/00769* (2013.01); *G07C 2009/00984* (2013.01)

(58) Field of Classification Search
CPC .... G07C 9/00111; G08B 21/02; G08B 21/22; G08B 21/0275; G08B 21/0286; G08B 21/0291; G08B 21/0423; G08B 21/0453; G08B 21/0461; G08B 21/0476; G08B 21/0484; G08B 21/0492; A61B 5/0022; A61B 5/0404; A61B 5/1117; A61B 5/0006; A61B 5/6806; A61B 5/01; A61B 5/7264; A61B 5/681; A61B 5/0488; A61B 5/0008; A61B 5/0402; A61B 5/0013; A61B 5/02055; A61B 5/0476; A61B 5/6807; A61B 5/1112; A61B 5/6891; A61B 5/6803; A61B 5/0077; A61B 5/002; A61B 5/1116

See application file for complete search history.

(56) References Cited

U.S. PATENT DOCUMENTS

| | | | | |
|---|---|---|---|---|
| 5,523,740 A | * | 6/1996 | Burgmann | G08B 21/22 340/539.1 |
| 5,561,331 A | * | 10/1996 | Suyama | E05B 19/0082 180/287 |
| 6,255,951 B1 | * | 7/2001 | De La Huerga | A61J 1/035 340/5.8 |
| D545,220 S | * | 6/2007 | Leung | D10/31 |
| 8,088,043 B2 | * | 1/2012 | Andren | A63B 24/00 368/10 |
| 8,115,621 B2 | * | 2/2012 | Rajala | G01S 1/042 340/539.11 |
| 9,007,195 B2 | * | 4/2015 | Ghabra | B60R 25/04 340/426.16 |
| 9,031,812 B2 | * | 5/2015 | Roberts | G08B 21/182 235/105 |
| 9,064,391 B2 | * | 6/2015 | Vardi | G08B 13/1463 |
| 2004/0233786 A1 | * | 11/2004 | Ting | G04B 47/00 368/2 |

(Continued)

*Primary Examiner* — Firmin Backer
*Assistant Examiner* — Adnan Aziz
(74) *Attorney, Agent, or Firm* — Volpe and Koenig, P.C.

(57) ABSTRACT

A wearable key fob is disclosed herein. The wearable key fob includes a wrist band including a slot and a key fob including a charging tab that fits into the slot of the wrist band; wherein the key fob is configured for vehicle operability and monitoring a user's health.

20 Claims, 3 Drawing Sheets

(56) References Cited

U.S. PATENT DOCUMENTS

| | | | | |
|---|---|---|---|---|
| 2005/0033515 A1* | 2/2005 | Bozzone | ............ | G01C 22/006 701/472 |
| 2007/0066088 A1* | 3/2007 | Rambosek | ............ | H05K 5/0278 439/37 |
| 2007/0179356 A1* | 8/2007 | Wessel | ............ | A61B 5/14532 600/300 |
| 2007/0290793 A1* | 12/2007 | Tran | ............ | G07C 9/00309 340/5.64 |
| 2008/0016738 A1* | 1/2008 | Talbott | ............ | A44C 5/0023 40/633 |
| 2008/0043575 A1* | 2/2008 | Fasciano | ............ | G04G 9/0076 368/13 |
| 2008/0045274 A1* | 2/2008 | Witkowski | ............ | G07C 5/008 455/569.2 |
| 2008/0309451 A1* | 12/2008 | Zellweger | ............ | G07C 9/00309 340/3.32 |
| 2009/0040874 A1* | 2/2009 | Rooney | ............ | A61J 7/0472 368/10 |
| 2009/0163322 A1* | 6/2009 | Andren | ............ | A63B 24/00 482/8 |
| 2009/0243791 A1* | 10/2009 | Partin | ............ | G08C 17/00 340/5.2 |
| 2011/0003665 A1* | 1/2011 | Burton | ............ | G04F 10/00 482/9 |
| 2011/0115624 A1* | 5/2011 | Tran | ............ | G06F 19/3418 340/540 |
| 2013/0204455 A1* | 8/2013 | Chia | ............ | G07C 5/008 701/1 |
| 2014/0180019 A1* | 6/2014 | Martinez | ............ | A61B 5/02055 600/301 |
| 2014/0266739 A1* | 9/2014 | Chen | ............ | B60Q 9/00 340/576 |
| 2014/0333417 A1* | 11/2014 | Sun | ............ | G09F 3/0297 340/10.1 |
| 2014/0358012 A1* | 12/2014 | Richards | ............ | A61B 5/02438 600/479 |
| 2015/0054628 A1* | 2/2015 | Roth | ............ | G06F 19/3418 340/10.4 |
| 2015/0061828 A1* | 3/2015 | Fischer | ............ | G07C 9/00007 340/5.61 |
| 2015/0182130 A1* | 7/2015 | Utter, II | ............ | A61B 5/0205 600/483 |
| 2015/0186609 A1* | 7/2015 | Utter, II | ............ | A61B 5/0022 600/301 |

* cited by examiner

WEARABLE KEY FOB

FIELD OF INVENTION

This application is related to vehicle electronics.

BACKGROUND

Cars increasingly require a programmable key fob for keyless entry or to initiate other functions relating to the vehicle, for example, unlocking car doors, opening the trunk/lift gate, activating a sliding door, and the like. Additionally, many active consumers use wearables to track their activity rate, health, and location. The ability to offer scalable functions into a wearable radio frequency (RF)/Bluetooth device reduces the clutter a consumer has to manage, for example, keys, watch, pedometer, and the like. There is an increasing need to combine the two technologies into an affordable product for easy access when the consumer's hands are full.

SUMMARY

A wearable key fob is disclosed herein. The wearable key fob includes a wrist band including a slot and a key fob including a charging tab that fits into the slot of the wrist band; wherein the key fob is configured for vehicle operability and monitoring a user's health.

BRIEF DESCRIPTION OF THE DRAWINGS

A more detailed understanding may be had from the following description, given by way of example in conjunction with the accompanying drawings wherein.

DETAILED DESCRIPTION

Figure 1:
FIG. 1 is a first example of a wearable key fob.

It is to be understood that the figures and descriptions of embodiments of a wearable key fob have been simplified to illustrate elements that are relevant for a clear understanding, while eliminating, for the purpose of clarity, many other elements found in typical vehicle systems. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The non-limiting embodiments described herein are with respect to a wearable key fob. Other electronic devices, modules and applications may also be used in view of these teachings without deviating from the spirit or scope as described herein. The wearable key fob may be modified for a variety of applications and uses while remaining within the spirit and scope of the claims. The embodiments and variations described herein, and/or shown in the drawings, are presented by way of example only and are not limiting as to the scope and spirit. The descriptions herein may be applicable to all embodiments of the wearable key fob although it may be described with respect to a particular embodiment.

A wearable key fob is extremely useful for the active consumer or the consumer on the go. The active consumer often uses wearables to track their activity rate, health, and location. Offering a wearable key fob with scalable functions reduces the clutter a consumer has to manage. For example, the consumer would only need one device to accommodate all of their needs. Additionally, the wearable key fob provides the consumer with easy access when their hands are full.

FIG. 1 is a first example of a wearable key fob. A wrist band 101 includes a key fob 102. The key fob 102 has a face 103 and a connector 104. The connector 104 attached the key fob 102 to the bracelet 101 to enable a user to wear the key fob 102. The key fob 102 is detachable from the wrist band 101 at the connector 104. The key fob 102 securely fits back into the wrist band 101 after it is removed.

The wrist band may be different colors and made of different materials to meet the individual consumer's personality and requirements. For example, the wrist band may be made of plastic, metal, ceramic, or the like.

Figure 2:
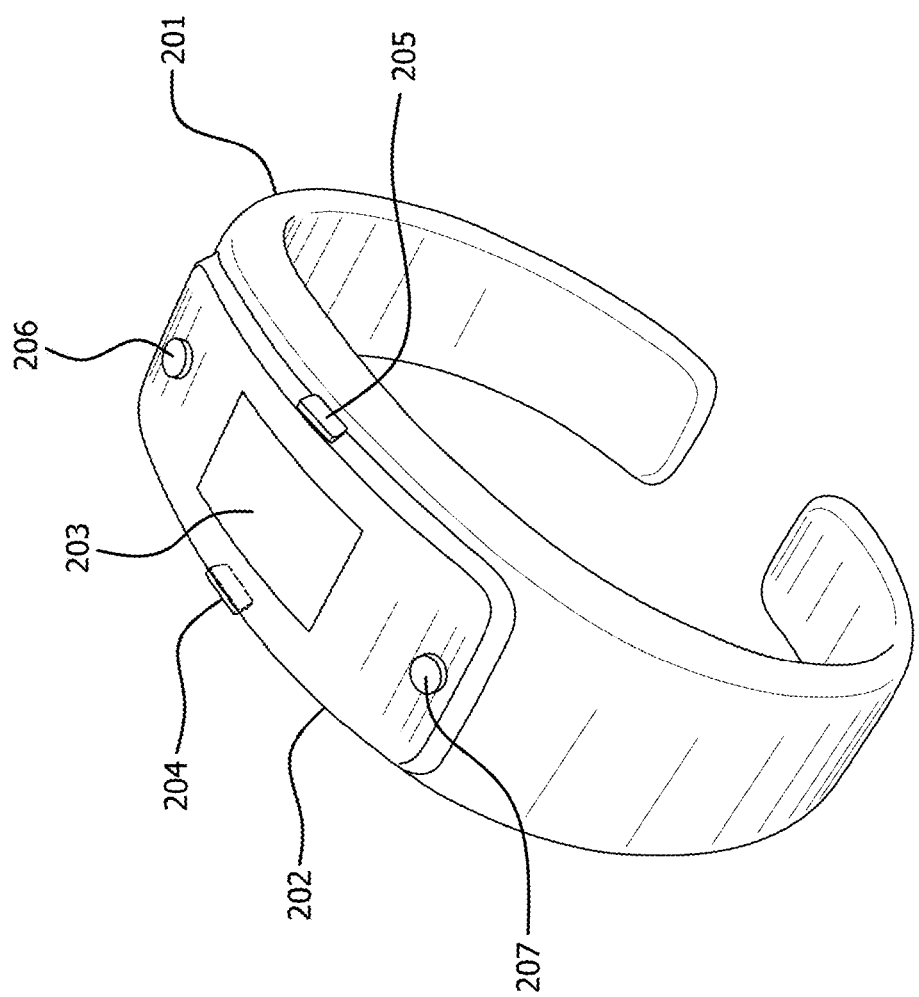
FIG. 2 is a second example of a wearable key fob.

FIG. 2 is a second example of a wearable key fob. A wrist band 201 includes a key fob 202. The key fob 202 has a display 203. The key fob 202 may also include several depressible buttons, for example, buttons 204-07. Button 204 may be used to display the time. Button 205 may be used to display fitness statistics, for example, number of steps, heart rate, calories burned, speed, mileage, and the like. Button 206 may be used to unlock the vehicle doors. Button 207 may be used to open the trunk/lift gate of the vehicle. When more than one of the buttons 204-207 are depressed simultaneously, additional functions may be triggered. For example, pushing buttons 206 and 207 simultaneously may trigger automatic start for the vehicle. In another example, pushing buttons 204 and 205 simultaneously may trigger the panic alarm for the vehicle. Additionally, the key fob 202 could activate a power lift gate, sliding doors, and the like. The key fob 202 is detachable from the wrist band 201. The key fob 202 may also have blue tooth capability to link to a user's cell phone to upload the fitness statistics.

Figure 3:
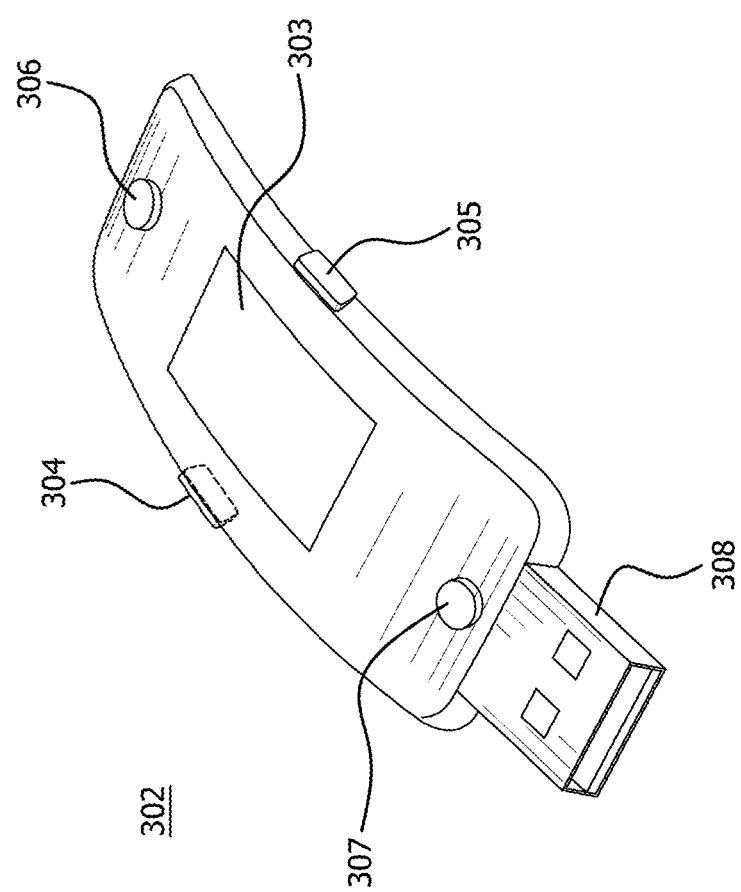
FIG. 3 is an example of the key fob removed from the wrist band.

FIG. 3 is an example of the key fob removed from the wrist band. The key fob 302 includes a display 303. The key fob 302 may also include several depressible buttons, for example, buttons 304-307. The key fob 302 may also include a charging tab 308. The charging tab 308 may connect to a power cell (not shown) to charge the key fob 302. The key fob 302 may need to be charged regularly depending on the number of functions embedded and how often they functions are utilized. The charging tab 308 is used to connect the key fob 302 to the wrist band. The key fob 302 is embedded with a vehicle start identification. The presence of the key fob 302 inside the vehicle will enable the vehicle to be turned on. The vehicle start identification, embedded in the key fob 302, will be the identification associated with the user's particular vehicle.

The key fob 302 may be compatible with the automobile's onboard computer system to display any data obtained during the consumer's use. For example, this may allow the consumer to view their daily activities and keep track of their fitness without having to connect the key fob 302 to another readable device. The key fob 302 utilizes a radio frequency (RF) signal, such as blue tooth, to communicate with the automobile's onboard computer system.

The key fob includes embedded devices. The embedded devices may be ARM, MIPS, Intel/Atom. The silicon embedded in the key fob may be manufactured by Broadcom, Marvell, STMicroelectronics, Samsung, Sigma Designs, and Texas Instruments. The embedded devices may include several components, for example, Random Access Memory (RAM), Flash (NAND/NOR) memory, a general purpose input/output (GPIO), a display, a light emitting diode (LED), an input, storage, radio frequency (RF) tuners, controllers, and a power management. The embedded devices may be managed using firmware/systems development and integration, manufacturing life cycle test development (for example, EVT/DVT/PVT), board/system bring-up support, and software architecture and design.

As described herein, the methods described herein are not limited to any particular element(s) that perform(s) any particular function(s) and some steps of the methods presented need not necessarily occur in the order shown. For example, in some cases two or more method steps may occur in a different order or simultaneously. In addition, some steps of the described methods may be optional (even if not explicitly stated to be optional) and, therefore, may be omitted. These and other variations of the methods disclosed herein will be readily apparent, especially in view of the description of the systems described herein, and are considered to be within the full scope of the invention.

Although features and elements are described above in particular combinations, each feature or element can be used alone without the other features and elements or in various combinations with or without other features and elements.

What is claimed:

1. A wearable device comprising:
   a wrist band including a slot; and
   a key fob including a charging tab that fits into the slot of the wrist band to connect the key fob to the wrist band and a plurality of depressible buttons located on an exterior surface of the key fob; wherein
   the key fob includes an integral transmitter and utilizes a radio frequency signal to communicate wirelessly,
   the key fob is configured for vehicle operability and monitoring a user's daily activities and health, and
   at least one of the depressible buttons of the plurality of depressible buttons is covered by the wrist band upon coupling of the wrist band with the key fob.

2. The wearable device of claim 1, wherein the key fob further includes a display.

3. The wearable device of claim 1, wherein the vehicle operability includes at least one of the following: starting a vehicle, activating a power lift gate, activating a panic button.

4. The wearable device of claim 1, wherein the key fob communicates with a vehicle's onboard computer system.

5. The wearable device of claim 4, wherein the key fob utilizes BLUETOOTH® to communicate with the vehicle's onboard computer system.

6. The wearable device of claim 1, wherein the monitoring of a user's health includes at least one of the following: monitoring heart rate, monitoring a number of steps the user takes, monitoring calories burned, and monitoring mileage.

7. The wearable device of claim 1, wherein the wrist band comprises at least one of the following: plastic, metal, and ceramic.

8. The wearable device of claim 1, wherein the key fob displays time.

9. The wearable device of claim 5, wherein the key fob utilizes BLUETOOTH® to communicate with the vehicle's onboard computer system to display a user's daily activities and health data obtained during the user's operation of the wearable key fob.

10. The wearable device of claim 1, wherein at least one depressible button faces exteriorly upon coupling of the wrist band with the key fob.

11. The wearable device of claim 1, wherein the at least one depressible button that is covered upon coupling of the wrist band with the key fob is located on a side wall of the key fob.

12. A wearable device comprising:
    a wrist band including a slot; and
    a key fob including a charging tab that fits into the slot of the wrist band to connect the key fob to the wrist band; wherein
    the key fob includes an integral transmitter and utilizes a radio frequency signal to communicate wirelessly,
    the key fob includes a vehicle start identification, wherein the presence of the key fob inside the vehicle will enable the vehicle to be turned on, and
    the key fob is configured for vehicle operability and monitoring a user's daily activities and health.

13. The wearable device of claim 12, wherein the key fob further includes a display.

14. The wearable device of claim 12, wherein the vehicle operability includes at least one of the following: starting a vehicle, activating a power lift gate, activating a panic button.

15. The wearable device of claim 12, wherein the key fob communicates with a vehicle's onboard computer system.

16. The wearable device of claim 15, wherein the key fob utilizes BLUETOOTH® to communicate with the vehicle's onboard computer system.

17. The wearable device of claim 12, wherein the monitoring of a user's health includes at least one of the following: monitoring heart rate, monitoring a number of steps the user takes, monitoring calories burned, and monitoring mileage.

18. The wearable device of claim 12, wherein the wrist band comprises at least one of the following: plastic, metal, and ceramic.

19. The wearable device of claim 12, wherein the key fob displays time.

20. The wearable device of claim 16, wherein the key fob utilizes BLUETOOTH® to communicate with the vehicle's onboard computer system to display a user's daily activities and health data obtained during the user's operation of the wearable key fob.

* * * * *